United States Patent [19]

Deutsch et al.

[11] Patent Number: 4,615,985
[45] Date of Patent: Oct. 7, 1986

[54] IMMOBILIZED PROTEIN ON NYLON FOR IMMUNOASSAY

[75] Inventors: Alice Deutsch, New York; Nancy Dorsey, Lynbrook, both of N.Y.

[73] Assignee: Genetic Diagnostics Corporation, Great Neck, N.Y.

[21] Appl. No.: 601,142

[22] Filed: Apr. 16, 1984

[51] Int. Cl.[4] .......................................... G01N 33/545
[52] U.S. Cl. ....................................... 436/531; 435/7; 435/181; 436/532; 436/548
[58] Field of Search ....................... 436/531, 532, 548; 435/181, 7

[56] References Cited

U.S. PATENT DOCUMENTS 3,843,324  10/1974  Edelman .................... 436/529 X
4,119,589  10/1978  Horn ........................... 435/181 X

OTHER PUBLICATIONS

"Applied Biochemistry and Bioengineering", vol. 3, Analytical Applications of Immobilized Enzymes and Cells, L. B. Wingard et al., eds., pp. 62-65, 80-83, Academic Press, New York, 1981.

Primary Examiner—Sidney Marantz
Attorney, Agent, or Firm—Sprung Horn Kramer & Woods

[57] ABSTRACT

A nylon matrix is partially hydrolyzed to form free amine end groups which are then linked to a protein molecule, e.g., an antigen or antibody, by a divalent radical which is the residue of a diimide molecule. The nylon carrying the protein can then be used in conventional manner in an immunoassay or an enzyme assay.

9 Claims, No Drawings

IMMOBILIZED PROTEIN ON NYLON FOR IMMUNOASSAY

The present invention relates to immobilizing proteins on a solid nylon matrix.

Proteins are involved in many immunochemical reactions and can be used in immunoassays. Thus, antibodies react with antigens, the antibodies and often the antigens both being proteins. Other proteins function as catalysts, in vivo or in vitro, e.g., enzymes such as $\beta$-galactosidases, phosphatases, and the like.

Such proteins are generally used in solution and, after the desired reaction, special separation measures are required. To obviate these, it has been proposed to link the protein to a solid matrix, i.e., to immobilize the protein, as on a stick. The stick is dipped into the reaction mix, reaction takes place on the surface of the stick, and the stick is withdrawn. However, it has been found that in the course of linking the protein to the stick, the protein loses its reactivity, i.e., it is denatured.

Attempts have been made to use various matrices. Tubes of nylon were etched with hydrochloric acid, activated with phosgene and then reacted with the enzyme trypsin, according to Horvath and Solomon, *Biotechnology and Bioengineering*, 14:885 (1972).

Enzymes were crosslinked to activated nylon by means of glutaraldehyde (Inman and Hornby, *Biochem J.*, 129:255 1972), Horvath, Sardi and Woods, *J. Applied Physiology*, 34:181 (1973).

Immobilization of other classes of protein was also investigated. Immunoglobulin can be immobilized more effectively by covalent coupling to nylon than by adsorption or covalent coupling to plastic (Hermann, John E., *Methods in Enzymology*, 73:239 (1981).

Numerous methods for the activation of nylon now exist. For a review of these procedures see: Hornby, W. E. and Morris, D. L., Modified Nylons in Enzyme Immobilization and Their Use in Analysis, in *Immobilized Enzymes, Antigens, Antibodies and Peptides;* Weetall, Howard H., ed., Marcel Dekker, Inc. New York, 1975 pp. 141; Sundaram, P.V. Potentials of Enzymes Attached to Nylon Tubes in Analysis, in *Biomedical Applications of Immobilized Enzymes and Proteins*, Vol. 2, T. M. S. Cheng, Ed., Plenum Press, 1977, p 317. Other attempts to immobilize proteins are disclosed in U.S. Pat. Nos. 4,206,286 and 4,253,844.

As noted, however, while the desired linkages did take place, the products did not retain the original level of reactivity of the protein before immobilization.

It is accordingly an object of the invention to immobilize protein while retaining its reactivity.

It is another object of the invention to immobilize the protein on a nylon matrix while retaining the protein reactivity.

These and other objects and advantages are realized in accordance with the present invention pursuant to which there is provided an immobilized protein comprising a partially hydrolyzed, still solid, nylon matrix, protein molecules, and divalent radicals linking the protein to the matrix, the divalent radicals being the residues of diimide molecules.

There is also provided a process for making such an immobilized protein comprising partially hydrolyzing a nylon matrix with N, N-dimethylaminopropylamine, terminating hydrolysis while the nylon is still solid, reacting the nylon with an acylating agent, then reacting the nylon with a diimide, and then reacting the product with the desired protein.

The nylon employed herein is preferably commercially available nylon 66 although nylon 6 and other polyamides are also suitable. The nylon is of conventional high molecular weight and may be in the form of powder, granules, beads, filter paper or a woven screen, although it is preferably in the form of tubes or sticks since they are easy to handle.

The nylon is subjected to initial hydrolysis, i.e., chain cleavage, to introduce reactive moieties. Such a moiety can be provided by effecting the cleavage with N,N-dimethylaminopropylamine. It can also be introduced by transamidation with other amines, e.g. primary and secondary aliphatic amines which may also carry a tertiary amino substituent, e.g., hexamethylenediamine, tetramethylenediamine, and the like.

The extent of introduction of reactive sites is related to the extent of cleavage and depends upon the amount of protein ultimately desired to be immobilized. It must be enough for practical purposes but not enough to solubilize the nylon or even to cause it to undergo a significant reduction in physical properties. Within those limits the precise degree of cleavage can be varied widely.

As a guide, however, as little as 1 hour contact between commercially available nylon 66 and dimethylaminopropylamine provided sufficient reactive sites for an eventual color response, as did overnight contact. In both instances the nylon still retained substantial physical strength. The reaction rate increases with temperature but above 70° C., oxidation of the nylon commences.

The hydrolysis or cleavage reaction can be effected in an inert solvent or it can be effected merely by contacting the nylon with a large excess of the cleavage agent, as by dipping or immersing nylon rods in the amine. Time and temperature vary inversely. About 1 hour at about 70° C. has proven satisfactory. The extent of hydrolysis can be calibrated from a few trial runs, monitoring with picrylsulfonic acid in the presence of sodium tetraborate, for example.

After the desired degree of hydrolysis, the solid nylon is removed. To ensure no further undesired cleavage, excess reagent is washed away.

For further activation it has been found to be advantageous to react with an acylating agent which presumably attaches itself to the residues from the N,N-dimethylaminopropylamine. Suitable acylating agents include carboxylic acid anhydrides and halides, e.g., acetic anhydride which has a high specificity and rapid reactivity even under mild conditions. Acetyl chloride, N,S-diacetyl-thioethanolamine, p-nitrophenyl bromoacetate, and even dicarboxylic acid anhydrides can be used.

Since the acylating agent reacts with the amine residues, it should be used in excess. Low temperatures for as little as an hour ensure complete reaction.

After washing away excess reagent, the nylon is reacted with a diimide which, it is believed, activates the carboxyl group. Again, the diimide is used in stoichiometric excess. A suitable diimide is 1-ethyl-3-(3-dimethylaminopropyl)-carbodiimide but other readily available diimides can be similarly employed. Excess diimide can be rinsed away.

The nylon matrix is now ready to receive the protein which apparently reacts with the diimide residues. Again, an excess of the protein is employed, as by dipping or immersing the nylon in a solution of the enzyme for several hours. The product is the desired immobilized protein with the protein activity effectively unimpaired.

As suitable proteins, there may be employed protein antigens or antibodies, especially monoclonal antibodies such as digoxin monoclonal antibody described in greater detail in Application Ser. No. 401,460, filed July 26, 1982, U.S. Pat. No. 4,477,576. However, any antigens including antigens linked to proteins or other antibodies used in immunoassays are suitable, e.g., immunoglobulins such as IgG, glycoproteins, hemoglobins, hormones, etc. Proteinaceous enzymes such as $\beta$-galactosidases, phosphatases, and the like, may also be employed.

The product, in the form of a rod, can be immersed in a test sample to permit the desired reaction to occur, dependent upon the composition of the sample. Thereafter, the test sample can be analyzed photometrically, fluorescently or the like, to determine the extent of reaction which took place, which is an index of the composition of the initial test sample.

The invention will be further described with reference to the following examples, wherein all parts are by weight unless otherwise expressed.

EXAMPLE #1

Nylon 66 lengths (Ain Plastics) were cut into 8 cm sticks. Peptide bonds were cleaved by amination using N,N-dimethylamino-propylamine (Aldrich Chemical Co.). Individual sticks were heated in 650 $\mu$l of the solvent at 70° C. for 1 hour. The sticks were rinsed with distilled water.

The extent of hydrolysis of the nylon sticks was monitored by immersing sticks in a 0.1% solution of 2,4,6-trinitrobenzene-sulphonic acid (Picryl sulfonic acid) in the presence of 0.1M sodium tetraborate. $NH_2$ groups of the activated nylon were acetylated by reacting the nylon with acetic anhydride (J. T. Baker Chemical Co.). Individual sticks were reacted with 650 $\mu$l of the anhydride for 1 hr. The reaction took place in an ice bath. After rinsing in distilled water, sticks were transferred to vials containing 650 $\mu$l of a 4% solution of 1-ethyl-3(3-dimethyl-amino-propyl) carbodiimide, HCl (Calbiochem-Behring). The sticks were incubated at room temperature for 30' and then rinsed in distilled water. The protein to be immobilized, in this example $\beta$-galactosidase, was prepared as a 20 $\mu$g/ml solution in phosphate buffered saline (PBS) pH 7.2. The activated sticks were incubated with the $\beta$-galactosidase at room temperature for 2 hrs. The sticks were then refrigerated overnight. Sticks were then quickly rinsed in 1M NaCl and stored in PBS. The sticks were then assayed for enzyme activity. One stick was incubated with the substrate methyl-umbelliferyl galactoside (100 $\mu$M in PBS) for 5 minutes at 37° C. The enzyme activity corresponded to 220 mU/stick, demonstrating that the enzyme in a nondenatured form was covalently coupled to the nylon stick.

EXAMPLE #2

The nylon sticks were prepared as described in Example 1 but the protein used was digoxin-bovine serum albumin (BSA) conjugate (from Immunotech).

The sticks were assayed for digoxin activity using the following protocol:

First, digoxin-BSA nylon sticks were incubated in 8M urea for 10 minutes at 37° C. to remove any physically adsorbed digoxin-BSA. Sticks were rinsed several times in PBS and then incubated in 1% gelatin in PBS for 10 minutes. Then the sticks were incubated for 15 minutes in a solution of digoxin monoclonal antibody coupled to $\beta$-galactosidase in 0.1% gelatin in PBS; the antibody was generated as described in application Ser. No. 516,483, filed July 22, 1983, now pending, and was coupled to $\beta$-galactosidase according to the method of Deelder and DeWater (1981, J. Histochem. Cytochem. 29:1273–1280). The sticks were washed in 0.1% gelatin in PBS and then incubated in 100 $\mu$M methyl umbelliferyl-$\beta$-D galactoside (MUG) for 5 minutes. Controls included untreated nylon sticks and theophylline-BSA coated nylon sticks. The results are shown in the following Table 1:

TABLE 1

| Stick | Fluorescence |
|---|---|
| digoxin-BSA | 88 |
| untreated | 24 |
| theophylline-BSA | 23 |

According to Table 1 the digoxin-BSA sticks gave the most fluorescence, demonstrating that this modified protein was covalently coupled to nylon and that the digoxin was not altered antigenically by the coupling procedure.

EXAMPLE #3

To test the procedure on another shape, 0.25 inch diameter nylon beads (Polymer Corp.) were treated as in Example 2. The beads were assayed as in Example 2. The results are shown in Table 2.

TABLE 2

| Bead | Fluorescence |
|---|---|
| digoxin-BSA | 80 |
| untreated | 34 |
| dilantin-BSA | 35 |

According to Table 2 the digoxin-BSA beads gave the most fluorescence, demonstrating that this modified protein was covalently coupled to the nylon beads.

EXAMPLE #4

The nylon sticks were prepared as described in Example #1 except the protein used was a monoclonal antibody to digoxin (described in Example #2).

The sticks were assayed for digoxin antibody activity using the following protocol. First, digoxin antibody sticks were "stripped" in 3M potassium thiocyanate for 10 minutes at 37° C. to remove any physically adsorbed antibody. Then the sticks were washed several times in 0.1% gelatin in PBS and incubated with digoxin-alkaline phosphatase conjugate (Immunotech) for 15 minutes at 37° C. The sticks were rinsed as before and incubated in p-nitrophenyl phosphate in 10% diethanolamine pH 9.8 for 10 minutes at 37° C. The results are shown in Table 3,

TABLE 3

| Dilution of Digoxin Alkaline-Phosphatase | Optical Density |
|---|---|
| 1:100 | .598 |
| 1:200 | .444 |
| 1:400 | .415 |
| 1:100* | .259 |

*Theophylline-BSA stick was used as a control.

The high optical density especially at 1:100 dilution of digoxin-alkaline phosphatase shows that the antibody was covalently coupled to the nylon sticks and was not denatured by the coupling procedure.

It is understood that the specification and examples are illustrative but not limitative of the present invention and that other embodiments within the spirit and scope of the invention will suggest themselves to those skilled in the art.

We claim:

1. An immobilized protein comprising a partially hydrolyzed still solid nylon matrix, protein molecules, and divalent radicals linking the protein to the matrix, the divalent radicals being the residues of diimide molecules, produced by partially hydrolyzing a nylon matrix, terminating hydrolysis while the nylon is still solid, reacting the nylon with an acylating agent, reacting the nylon with a diimide, and then reacting the product with a protein.

2. An immobilized protein according to claim 1, wherein the protein comprises an enzyme.

3. An immobilized protein according to claim 1, wherein the protein comprises an antigen or antibody or is linked to an antigen.

4. An immobilized protein according to claim 1, wherein the protein comprises a monoclonal antibody.

5. An immobilized protein according to claim 1, wherein the nylon was partially hydrolyzed by N,N-dimethylaminopropylamine.

6. In an immunoassay wherein an antigen and an antibody are caused to interact, and the extent of interaction is monitored, the improvement wherein the antigen or antibody is employed in immobilized form according to claim 1.

7. The method according to claim 6, wherein the immobilized substance is a monoclonal antibody.

8. A prepared matrix ready to immobilize a protein, produced by partially hydrolyzing a nylon matrix with N,N-dimethylaminopropylamine, terminating hydrolysis while the nylon is still solid, reacting the nylon with an acylating agent, and then reacting the nylon with a diimide.

9. An intermediate in the preparation of an immobilized protein, produced by partially hydrolyzing a nylon matrix with N,N-dimethylamino-propylamine, terminating hydrolysis while the nylon is still solid, and reacting the nylon with an acylating agent.

* * * * *